United States Patent [19]

Wrasidlo et al.

[11] Patent Number: 4,853,128
[45] Date of Patent: Aug. 1, 1989

[54] NON-DISTORTING SEPARATOR FOR AUTOCLAVABLE MEMBRANE STACKS

[75] Inventors: Wolfgang J. Wrasidlo, LaJolla; Frieder K. Hofmann, Oceanside; Dirk M. DeWinter, Vista, all of Calif.

[73] Assignee: Brunswick Corporation, Skokie, Ill.

[21] Appl. No.: 183,056

[22] Filed: Apr. 19, 1988

[51] Int. Cl.$^4$ ................................................ B01D 13/04
[52] U.S. Cl. ............................ 210/636; 264/342 RE; 429/19
[58] Field of Search ................ 264/342 RE; 210/651, 210/636; 429/19

[56] References Cited

U.S. PATENT DOCUMENTS 4,048,383  9/1977  Clifford ................................. 429/19
4,291,470  9/1981  Newman ....................... 264/342 RE
4,715,960  12/1987  Thompson ........................... 210/651

Primary Examiner—Frank Sever
Attorney, Agent, or Firm—Waldron & Associates

[57] ABSTRACT

In applications involving interleaving membranes with separators, for bioreactors, dialyzers, and membrane filters and the like, shrinkage of the separator, preferably made of polypropylene, polyamides, or polyethylene terephthlate fiber web, is avoided, and the need for the use of exotic and expensive fluorinated hydrocarbon polymer materials for such separators is avoided by subjecting the separator to untensioned heating at temperatures of from about b 120 l degrees C., up to a temperature less than the glass transition or melting temperature of the polymer web under wet steam at a pressure of from about 1.0 to about 2.0 atmospheres for a time of at least about 20 minutes.

8 Claims, No Drawings

NON-DISTORTING SEPARATOR FOR AUTOCLAVABLE MEMBRANE STACKS

BACKGROUND OF THE INVENTION

Sheet membranes are employed in a diversity of uses which involve placing the sheets in a stacked or interleaved or layered arrangement or configuration wherein the space between layers, whether between two membranes or between a membrane and some other material, is established and maintained by a sheet separator. In practice there are a wide number of materials employed as separators, each of which may be available in a variety of forms.

By way of example, membrane separators are made of polypropylene, polyamides, polyesters, particularly polyethylene terephthalate, and the like. Such separators may be formed into a suitable sheet form for use in the form of woven or non-woven fabric or webs, perforated film, macroporous membranes, or even as sintered or partially fused particulate forms.

In such applications, the layered construction may be in flat, planar form, wound into a spiral configuration, or other arrangements involving plural layers where one or more layers is required to be a separator for other adjacent layers.

In many applications of such configurations, there is a need for sterilization of the final assembly before use. Among such applications are sterile filtration, particularly those involving food treatment or pharmaceutical products, dialysis, particularly hemodialysis and other biological and medical techniques, and in the use of membranes in bioreactors to confine living cells or organisms in the production of biological products.

It is usual to subject such membrane assemblies to autoclaving to achieve sterile conditions. By the usual conditions of high temperature and pressure, typically about 120 to about 130 deg C., at about 1.0–2.0 atmospheres of steam, it is generally rather rapid and convenient to achieve effective sterilization, although it may be necessary to limit the temperature of the steam to avoid damage to temperature sensitive materials. This can generally be offset by increased retention time at a lower temperature.

Other techniques for sterilization, i.e., cold chemical sterilizing and the like, are generally not effective, often taking many hours, and often cannot be employed at all without damage to the materials used in the stack assembly or difficulty in removing the sterilizing agent after the procedure.

It is well known to the art that most of the common materials of interest as separators in such assemblies are susceptible to a material degree of shrinkage upon autoclaving. It is a general problem which requires that the assembly be formed in such a fashion that the shrinkage is allowed for, so that the configuration is appropriate after the autoclaving operation. In some sheet membrane - separator assemblies this can be achieved with little difficulty.

There are a number of occasions where the desired assemblies require a construction that does not admit of leaving allowances for shrinkage. This most often arises in stack assemblies involving the use of a plurality of membrane layers, where each layer is separated from its neighbors by a separator sheet layer, and where the assembly requires sealing at the edges. This type of structure, whether in flat stack configurations or in spiral wound assemblies, is of considerable and increasing interest for bioreactor applications, biological dialysis and filtration applications, and the like.

In such structures, the required allowances for shrinkage of the separator cannot be made without compromising the structure in unacceptable ways.

On the other hand, if no allowance is made for the shrinkage, the structure will be materially distorted and damaged by the effects of shrinkage when the assembly is autoclaved.

Since neither of these possibilities can be tolerated, it is usual to select separator materials which are not susceptible to such distortions when subjected to autoclaving. It has often been attempted to employ pre-shrunk materials, some of which are available, but even these types of materials have been observed to retain a material susceptibility to shrinkage. The usual preshrinking procedure is to subject the screen material to high temperature "annealing" under tension. Because these techniques are not generally sufficient, it is the current practice in the manufacture of membrane stacks to employ expensive and exotic materials to avoid the shrinkage problems. For example, such materials as fluorinated hydrocarbon polymer porous sheet materials are frequently employed in such applications.

These materials are expensive, often to the deree that the cost of the separator components may exceed the total costs of the other components of the assembly by a wide margin.

OBJECTS OF THE INVENTION

It is accordingly an object of the present invention to provide a method of making such assemblies whereby less expensive separators may be employed without substantial shrinkage when subjected to autoclaving sterilization.

It is another object of the present invention to treat such separators to prevent excessive shrinkage when subjected to autoclaving.

It is also an object of the present invention to provide membrane - separator assemblies which are not subject to distortion or damage when subjected to autoclaving.

Another object of the present invention is to provide means whereby polypropylene, polyamides, and polyester, particularly polyethylene terephthlate, separator screens can be effectively employed in shrinkage sensitive membrane stack constructions without subjecting the stack to unacceptable levels of distortion or damage when the assembly is subjected to autoclaving for sterilization.

SUMMARY DESCRIPTION OF THE INVENTION

In applications involving interleaving membranes with separators, for bioreactors, dialyzers, and membrane filters and the like, distortions and damage associated with shrinkage of the separator in use is avoided, and the need for the use of exotic and expensive polymer materials for such separators is avoided by subjecting the separator to untensioned heating at temperatures of from about 120 to about 130 degrees C., under wet steam at a pressure of from about 1.0 to about 2.0 atmospheres for a time of at least about 10, preferably at least about 20 minutes.

DETAILED DESCRIPTION OF THE INVENTION

In the present invention, the separator materials of interest are highly porous webs of materials having a stable and controlled thickness, suitable for serving as separators in membrane stack assemblies. The separator may be woven or nonwoven, usually monofilament, fabric, perforated film, or the like. The separators are made of polymer materials having the physical properties compatible with the intended utilization of the membrane - separator stack assembly. Thickness of the web will ordinarily be on the order of about 250 to about 500 micrometers, and the openings in the web will generally be of about the same or similar dimensions.

The separator is desirably, and preferably made of inexpensive materials, such as polypropylene, polyamides, or polyethylene terephthlate fibers and yarns. Such polymers are widely available in woven and flocked or felted webs in a diversity of sizes, thicknesses, and physical properties. Such materials are also known to be highly susceptible to shrinkage when subjected to autoclaving.

In the present invention, the separator screen materials and the associated membranes are subjected to a pre-shrinking procedure which produces such screen materials having a very low residual shrinkage, when assembled as separators in membrane stack assemblies, substantially the same as the degree of shrinkage of the membrane components of the assembly.

The separator materials and membranes in the present invention are heated in untensioned form at a temperature of about 120 to 130 degrees C., but in all events a temperature below the glass transition temperature or the melting temperature of the polymer material, at a pressure of from about 1.0 to 2.0 atmospheres of wet steam, for a period of from about 20 to about 60 minutes, preferably about 20 to about 30 minutes.

The utilization of wet saturated steam, and the presence of moisture, has been observed to be essential to the effectiveness of the pre-shrinking operation. While the reasons for this are not fully understood, it appears that the moisture swells the polymer to some slight degree at the conditions imposed, at least at the surface, so that some degree of stress relief may be effected. After the treatment, the subsequent susceptibility to shrinkage is materially reduced, and thus an irreversable effect is achieved. Neither dry steam nor dry annealing processes produce the permanent irreversible shrinkage achieved by the present procedure. It has also been observed that the irreversible effect is not obtained, or fully obtained, if the procedure is conducted under tension, as is commonly employed, and the procedure thus is to be conducted without the application of any material tensioning.

It can be noted that neither the maximum duration of the procedure, nor the magnitude of the pressure is of any material consequence in the present invention so long as the minimums defined herein are met. Longer duration or higher pressures than those suggested herein are not likely to make any material contribution to the effectiveness of the procedure, and are thus not recommended and certainly not preferred, but are not a detriment to the procedure.

Since the pre-shrink treatment is conducted prior to the assembly of the membrane and separator components into the form for their intended use, and is not intended to replace or substitute for subsequent sterilization, there is no requirement that the materials be handled aseptically during assembly. To the extent the procedure of the preshrinking of the material does sterilize the web, such is neither the purpose or intent of the procedure. It is the substantial reduction or elimination of shrinkage in subsequent autoclaving operations which is the greatest advantage of the procedure, and should not be considered a replacement therefore.

The treated screen material is cut to the desired dimensions and fitted into the appropriate membrane stack assembly for the intended use. The final stack assembly should thereafter be autoclaved prior to use, and if appropriate to the nature of the use, the assembly may be repeatedly autoclaved thereafter as needed. Sterility can thus be achieved even with the inexpensive and yet fully functional separator materials of the present invention without distortion or disruption of the stack assembly.

The conditions of the autoclaving may be substantially the same as those of the pre-shrink treatment, or any other autoclaving conditions desired, so long as the temperature is not so high that the material of the stack assembly does not soften or melt. The polypropylene, polyamides, and polyester web materials are generally temperature stable at temperatures commonly employed for autoclaving, i.e., up to about 130 degrees C. The temperature limits of the membrane stack assembly may be determined in some cases by the temperature properites of the membrane component or other elements of the assembly.

The separators prepared in accordance with the present invention may be employed and used for membrane stack assemblies for sterile filtration, particularly those involving food treatment or pharmaceutical products, dialysis, particularly hemodialysis and other biological and medical techniques, and in the use of membranes in bioreactors to confine living cells or organisms in the production of the biological products.

EXAMPLE

A stacked membrane bioreactor for the culturing of live cells, particularly hybridomas used in the production of monoclonal antibodies is formed by the following procedures:

A woven polypropylene monofilament fabric separator material, having openings in the weave of about 250 micrometers, and an average thickness of about 250 micrometers, is heated to a temperature of 122 degrees C. with no tension under wet steam at a pressure of about 1 atmosphere for a period of thirty minutes. The material is then cooled to ambient, and is cut into squares of twelve inches on a side.

A hydrophilic polysulfone microporous membrane sheet, also subjected to autoclaving prior to use, having a limiting pore size of 0.2 micrometers in diameter, is cut into squares twelve inches on a side.

The separator and membrane sheets are interleaved, and each second adjacent pair of the membranes are sealed with an adhesive on two sides, with the alternating adhesive bonding being on all four sides, thus defining flow pathways through the stack alternating with closed chambers. Each such chamber is provided with a port to permit the introduction of cells and an oxygen supply must be provided as well. Each adjacent pair of membranes is separated by a separator. The open ends of the unsealed edges are manifolded into a reaction vessel.

The stack assembly installed in its reaction vessel is autoclaved to sterilize the system. No distortion is observed.

A flow of nutrient, through the inlet manifold and then through the flow pathways of the stack, and an oxygen supply are started. Cells are then introduced into the closed chambers of the reactor. Nutrient diffuses through the membranes from the nutrient flow pathways of the stack into the cell chambers, and nourishes the cells. Partially spent nutrient, carbon dioxide, and cell products, including monoclonal antibody, diffuse through the membrane from the cell chamber into the nutrient flow path, where the materials pass into an outlet manifold and out of the system where the monoclonal antibody is recovered. No septic contamination is observed in the system.

While the present invention finds its greatest utility in preshrinking of separator materials, it has been observed to be effective and of use in preshinking some membranes as well. The procedure does not materially alter the effective pore size of such membranes.

What is claimed is:

1. In the method including forming an autoclavable assembly of interleaved membranes and sheet separators comprising forming a stack of membranes interleaved with polymer web separators, the improvement comprising subjecting at least said separators to preshrinking prior to the formation of said stack by heating without tension at a temperature of from about 120 to about 130 degrees C. with wet steam at a pressure of from about 1.0 to 2.0 atmospheres for a time of from about 10 to about 60 minutes to produce an irreversible shrinkage of said separators.

2. The method of claim 1 wherein said sheet separators are polypropylene and said heating is conducted at a temperature from about 121 to about 125 degree C.

3. The method of claim 1 wherein said time is from about 20 to about 30 minutes.

4. The method of claim 1 wherein said separators are made of a polymer material selected from the group consisting of polypropylene and polyester and said heating is conducted at a temperature from about 120 to about 130 degree C.

5. The method of claim 1 wherein said separators are woven.

6. The method of claim 1 wherein said separators are nonwoven fabric.

7. An autoclavable stack assembly of interleaved membranes and porous sheet separators comprising the product of the process of claim 1.

8. A method comprising forming a sterile assembly of interleaved polymer components comprised of membranes and separators, wherein at least the separator component is susceptible to a deleterious degree of shrinkage at the conditions of sterilization by autoclaving, including A. heating each of the said components susceptible to a deleterious degree of shrinkage, under substantially untensioned conditions, to a temperature of at least about 120 degrees Centigrade, to a temperature below the Tg of the polymer of said component, in the presence of wet steam at a pressure of at least about 0.5 atmospheres, for a time sufficient to effect an irreversible shrinkage of each such component;

B. assembling said components into said assembly, whereby relative movement between at least some of the edges thereof is constrained; and C. autoclaving said assembly to sterility at a temperature sufficient to sterilize said assembly but not exceeding the temperature of step A.

* * * * *